（12） United States Patent
Hibner et al.

(10) Patent No.: US 11,076,927 B2
(45) Date of Patent: Aug. 3, 2021

(54) USAGE AND PROCEDURE COUNTER FOR SURGICAL TOOLS

(71) Applicant: Ethicon LLC, Guaynabo, PR (US)

(72) Inventors: John A. Hibner, Mason, OH (US); Andrew Crews, Maineville, OH (US)

(73) Assignee: Cilag GmbH International

( * ) Notice: Subject to any disclaimer, the term of this patent is extended or adjusted under 35 U.S.C. 154(b) by 150 days.

(21) Appl. No.: 16/189,343

(22) Filed: Nov. 13, 2018

(65) Prior Publication Data

US 2020/0146765 A1 May 14, 2020

(51) Int. Cl.
| A61B 34/00 | (2016.01) |
| A61B 34/30 | (2016.01) |
| A61B 90/00 | (2016.01) |
| G16H 40/40 | (2018.01) |
| A61B 18/14 | (2006.01) |

(52) U.S. Cl.
CPC ............. *A61B 34/71* (2016.02); *A61B 34/30* (2016.02); *A61B 18/1442* (2013.01); *A61B 2090/0803* (2016.02); *A61B 2560/0266* (2013.01); *G16H 40/40* (2018.01)

(58) Field of Classification Search
CPC combination set(s) only.
See application file for complete search history.

(56) References Cited

U.S. PATENT DOCUMENTS

| 9,730,717 B2 | 8/2017 | Katsuki |
| 2007/0156285 A1* | 7/2007 | Sillman ................... A61B 34/30 |
| | | 700/245 |
| 2012/0203269 A1* | 8/2012 | Katsuki ................... A61B 90/98 |
| | | 606/205 |
| 2013/0331860 A1* | 12/2013 | Komuro ................... A61B 34/30 |
| | | 606/130 |
| 2017/0065365 A1* | 3/2017 | Schuh ..................... A61B 34/30 |
| 2017/0156285 A1 | 6/2017 | Ammerlaan et al. |
| 2017/0273542 A1* | 9/2017 | Au ......................... A61B 1/00133 |
| 2019/0274769 A1 | 9/2019 | Perdue |

FOREIGN PATENT DOCUMENTS

| WO | 2016144937 A1 | 9/2016 |
| WO | WO-2016144937 A1 * | 9/2016 ............. B25J 9/1694 |

OTHER PUBLICATIONS

ISR-WO for PCT/IB2019/059510, which claims priority to the present application, dated Jan. 27, 2020.

* cited by examiner

*Primary Examiner* — Rex R Holmes
*Assistant Examiner* — Jennifer L Ghand
(74) *Attorney, Agent, or Firm* — Vorys, Sater, Seymour and Pease LLP

(57) ABSTRACT

A method of operating a surgical tool includes mounting the surgical tool to a tool driver. The surgical tool includes one or more drive cables movable to actuate an end effector, and one or more segments are defined along a portion of at least one of the one or more drive cables and each segment exhibits a usage value. Usage of the drive cables is monitored with a computer system in communication with the tool driver, and the usage value of one or more of the segments is altered based on usage of the surgical tool.

20 Claims, 8 Drawing Sheets

USAGE AND PROCEDURE COUNTER FOR SURGICAL TOOLS

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more intuitive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system to selectively move particular drive cables that articulate the end effector to desired angular positions and configurations.

During use, the drive cables are repeatedly subjected to applied loading and unloading forces that, over time, can weaken the material and cause fatigue. Although rare, the drive cables can fail following prolonged usage. If a drive cable fails mid-operation, the surgical procedure may need to be placed on hold while the surgical tool is repaired or replaced, thus introducing unanticipated delay. In a worst-case scenario, mid-operation drive cable failure might inadvertently injure a patient. Accordingly, it may be beneficial to track the remaining useful life of a surgical tool to mitigate or entirely prevent drive cable failure during use.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to robotic surgical systems and, more particularly, to monitoring and reporting operational usage of a surgical tool to avoid inefficient operation and/or prevent mid-operation failure.

Embodiments discussed herein describe methods of operating a surgical tool, where the surgical tool includes one or more drive cables movable to actuate an end effector. One example method includes mounting the surgical tool to a tool driver, wherein one or more segments are defined along a portion of at least one of the one or more drive cables and each segment exhibits a usage value. Usage of the drive cables may then be monitored with a computer system in communication with the tool driver, and the computer system may alter the usage value of at least one of the segments based on usage of the surgical tool.

In some embodiments, tensile loading on the drive cables may be measured with a torque sensor in communication with the computer system, and the usage value of specific segments may be increased based on tensile data received from the torque sensor. In some embodiments, rotational output of one or more drive inputs of the surgical tool or one or more drivers of the tool driver may be measured with a rotary encoder in communication with the computer system. The linear distance traveled by the segments may then be determined based on rotational output data received from the rotary encoder, and the usage value of specific segments may be increased based on the linear distance traveled. The computer system may also be configured to aggregate usage value increments to determine a current usage value of the segments. Based on the current usage value of the segments, the computer system may calculate when at least one of the drive cables will fail, issue an alert when the current usage value reaches a predetermined usage value, and prevent the surgical tool from being used in a subsequent procedure when the current usage value reaches a predetermined usage value.

FIGS. 1-5 illustrate the structure and operation of an example robotic surgical system and associated components thereof. While applicable to robotic surgical systems, it is noted that the principles of the present disclosure may equally or alternatively be applied to non-robotic surgical systems, without departing from the scope of the disclosure.

Figure 1:
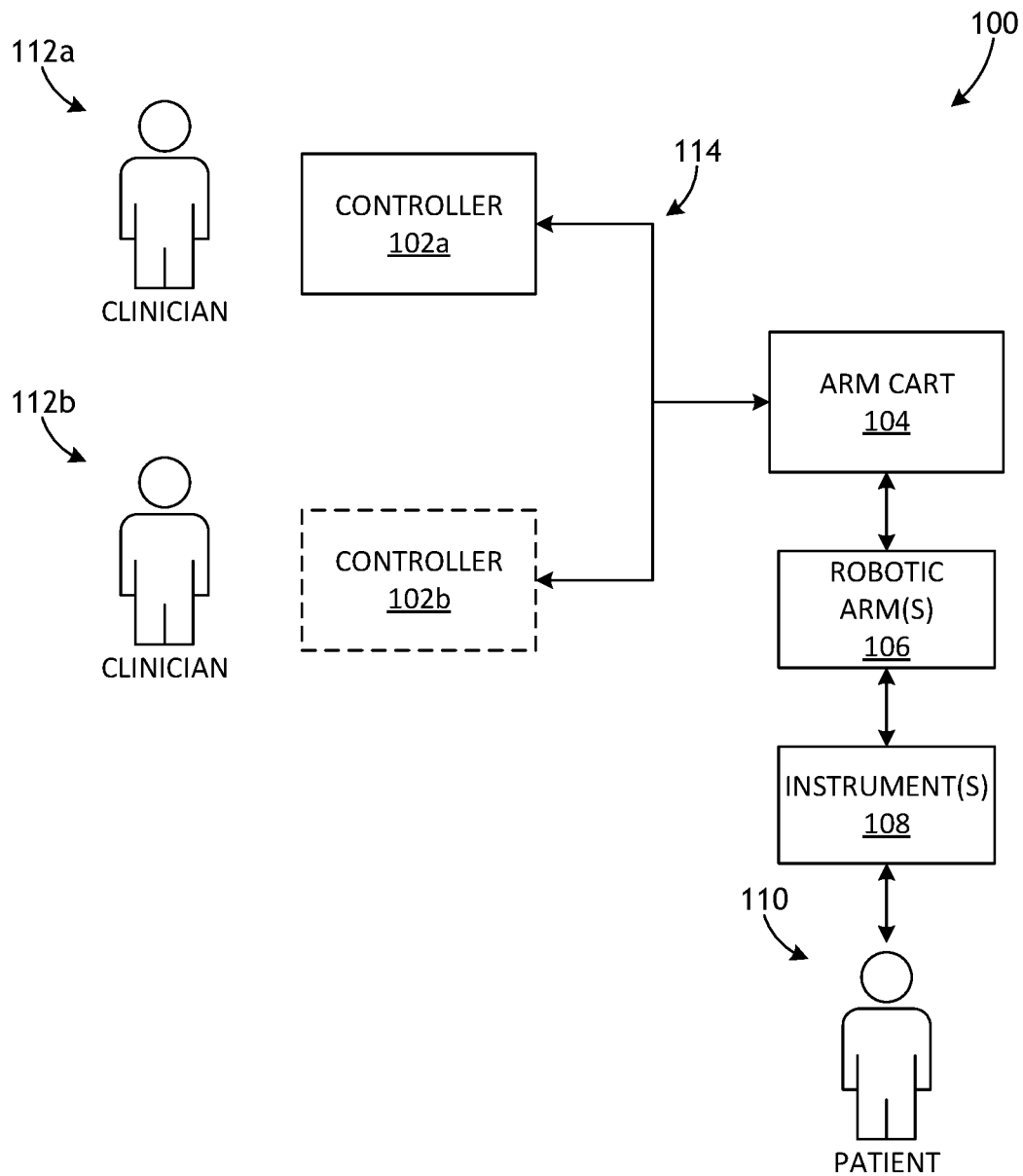
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one master controller 102a and at least one arm cart 104, although the arm cart 104 is not necessarily required. The arm cart 104 may be mechanically and/or electrically coupled to a robotic manipulator and, more particularly, to one or more robotic arms 106. Each robotic arm 106 may include and otherwise provide a tool driver where one or more surgical instruments or tools 108 may be mounted for performing various surgical tasks on a patient 110. Operation of the robotic arms 106, the corresponding tool drivers, and the associated tools 108 may be directed by a clinician 112a (e.g., a surgeon) from the master controller 102a.

In some embodiments, a second master controller 102b (shown in dashed lines) operated by a second clinician 112b may also direct operation of the robotic arms 106 and tools 108 in conjunction with the first clinician 112a. In such embodiments, for example, each clinician 102a,b may control different robotic arms 106 or, in some cases, complete control of the robotic arms 106 may be passed between the clinicians 102a,b. In some embodiments, additional arm carts (not shown) having additional robotic arms (not shown) may be utilized during surgery on a patient 110, and these additional robotic arms may be controlled by one or more of the master controllers 102a,b.

The arm cart 104 and the master controllers 102a,b may be in communication with one another via a communications link 114, which may be any type of wired or wireless communications link configured to carry suitable types of signals (e.g., electrical, optical, infrared, etc.) according to any communications protocol. In some applications, for example, there is a tower with ancillary equipment and processing cores designed to drive the robotic arms 106. The communications link 114 may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network.

Figure 2:
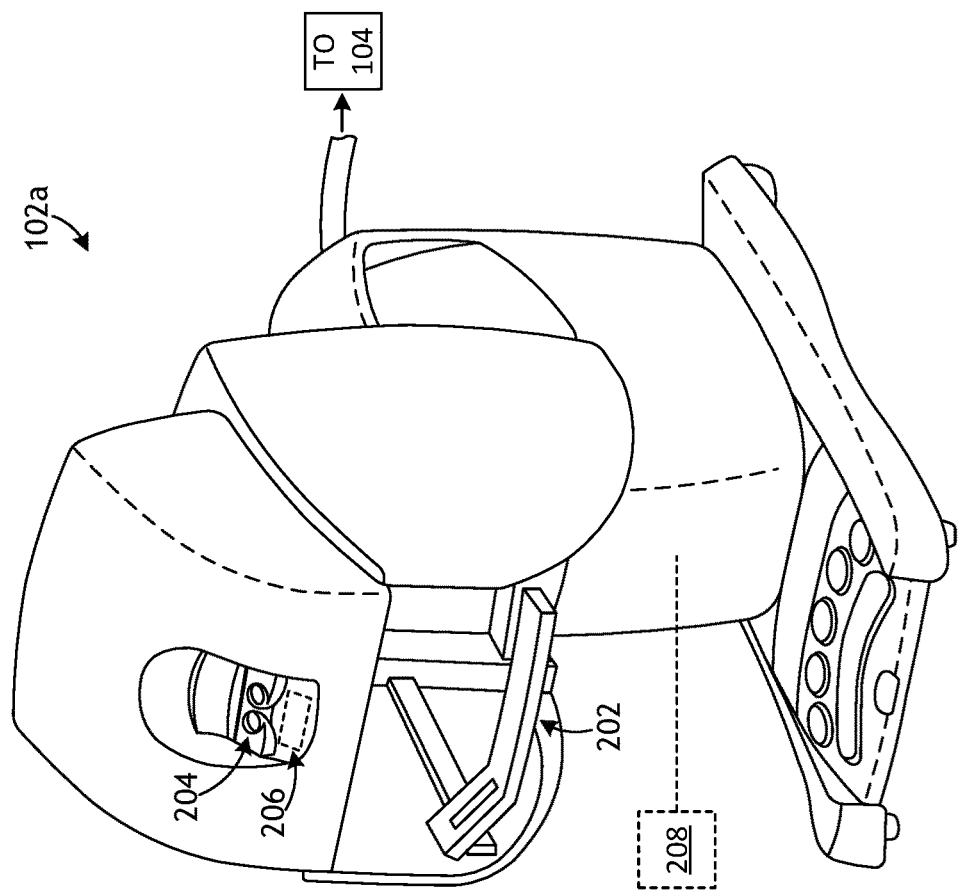
FIG. 2 is an example embodiment of the master controller of FIG. 1 that may be used to operate a robotic arm slave cart.

FIG. 2 is an example embodiment of the master controller 102a that may be used to operate a robotic arm slave cart, such as the arm cart 104 of FIG. 1. The master controller 102a and its associated arm cart 104, as well as their respective components and control systems, are collectively referred to herein as a "robotic surgical system." The master controller 102a can include a support 202 on which the clinician 112a,b (FIG. 1) can rest his/her forearms while gripping two physical controllers (e.g., a joystick, exoskeletal gloves, a master manipulator, etc.), one in each hand. The physical controllers may be manipulated in space while the surgeon views the procedure via a stereo display 204. The physical controllers generally comprise manual input devices designed to move in multiple degrees of freedom, and which often further have an actuatable handle for actuating a surgical tool (e.g., the surgical tool(s) 108 of FIG. 1), for example, for opening and closing opposing jaws, applying an electrical potential to an electrode, or the like.

In the illustrated example, the master controller 102a further includes an optional feedback meter 206 viewable by the clinician 112a,b via the display 204 to provide the surgeon with a visual indication of the amount of force being applied to the surgical tool (i.e., a cutting instrument or dynamic clamping member). Other sensor arrangements may be employed to provide the master controller 102a with an indication of other surgical tool metrics, such as whether a staple cartridge has been loaded into an end effector or whether an anvil has been moved to a closed position prior to firing, for example.

The master controller 102a may further include or otherwise communicate with a computer system 208 that may help control and operate the master controller 102a. The embodiments described herein may be implemented, at least in part, using the computer system 208, which may be characterized as a digital data processing and programmable system. The computer system 208 may include one or more processors operable to control operation of the computer system 208, and may further include one or more memories that provide temporary storage for code to be executed by the processor(s) or for data acquired from one or more sensors, storage devices, and/or databases.

Figure 3:
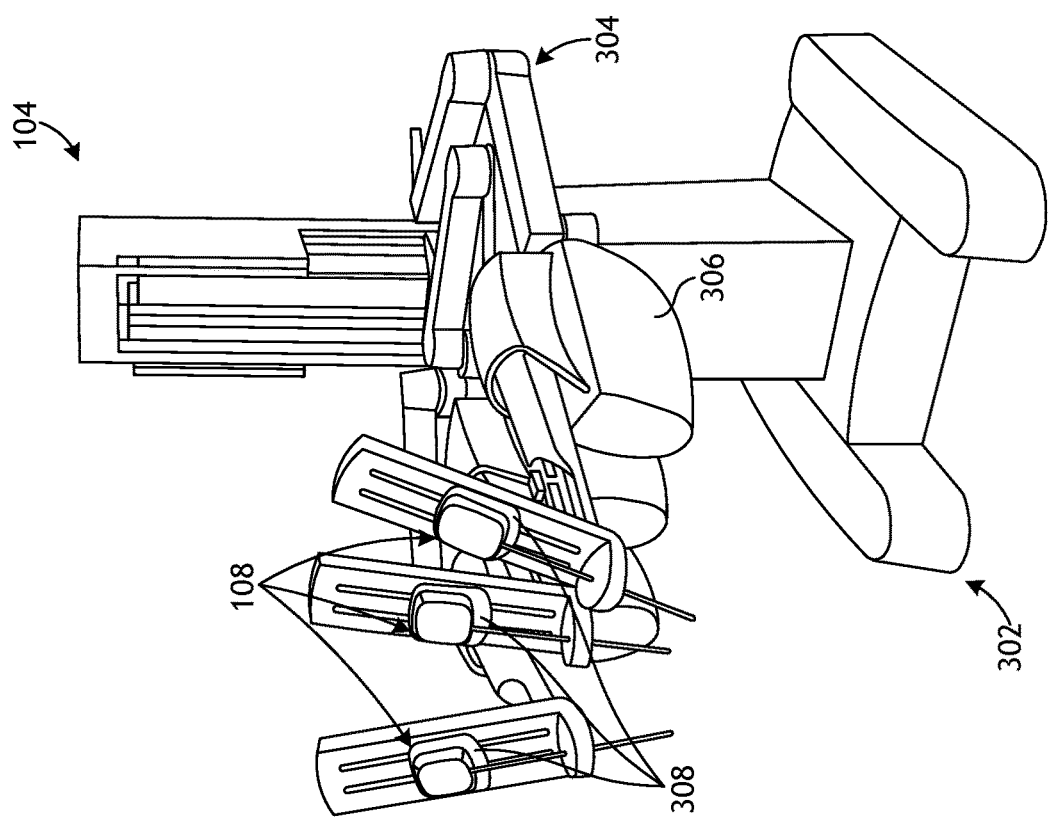
FIG. 3 depicts an example embodiment of the robotic arm cart of FIG. 1 used to actuate a plurality of surgical tools.

FIG. 3 depicts an example embodiment of the robotic arm cart 104 used to actuate a plurality of surgical tools 108. As illustrated, the robotic arm cart 104 may include a base 302 that supports a series of manually articulable linkages, generally referred to as set-up joints 304 and a robotic manipulator 306. In the illustrated embodiment, three surgical tools 108 are mounted to corresponding tool drivers 308 provided by the robotic manipulators 306. Each tool driver 308 may include one or more drivers or motors used to interact with a corresponding one or more drive inputs of the surgical tools 108. As discussed below, actuation of the drive inputs causes the associated surgical tool 108 to operate.

Figure 4:
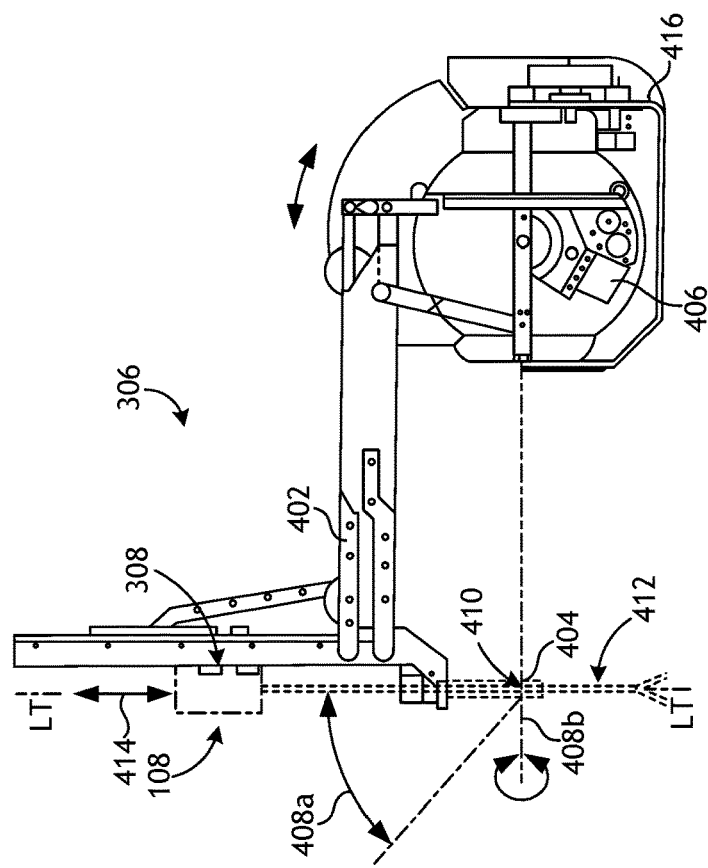
FIG. 4 is a side view schematic diagram of an example embodiment of the robotic manipulator of FIG. 3.

FIG. 4 is a side view schematic diagram of an example embodiment of the robotic manipulator 306. As illustrated, the robotic manipulator 306 may include linkage 402 that constrains movement of the surgical tool 108 coupled thereto at a tool driver 308. The linkage 402 includes rigid links coupled by rotational joints in a parallelogram arrangement so that the surgical tool 108 is able to rotate around a point 404 in space. The linkage 402 may be driven by a series of motors 406 that selectively move the linkage 402 in response to commands from a processor of a control system. The motors 406 may also be employed to manipulate the surgical tool 108.

The parallelogram arrangement of the linkage 402 constrains rotation to pivoting about a first axis 408a, referred to as the "pitch axis." The links supporting the parallelogram linkage 402 are pivotally mounted to set-up joints 304 (FIG. 3) so that the surgical tool 108 further rotates about a second axis 408b, referred to as the "yaw axis." The pitch and yaw axes 408a,b intersect at a remote center 410, which is aligned along a shaft 412 of the surgical tool 108.

The surgical tool 108 may have further degrees of driven freedom as supported by the robotic manipulator 306, including sliding motion of the surgical tool 108 along a longitudinal tool axis "LT-LT". As the surgical tool 108 slides (translates) along the longitudinal tool axis LT-LT relative to the robotic manipulator 306 (arrow 414), the remote center 410 remains fixed relative to a base 416 of the robotic manipulator 306. Hence, the entire robotic manipulator 306 is generally moved to re-position the remote center 410.

Figure 5:
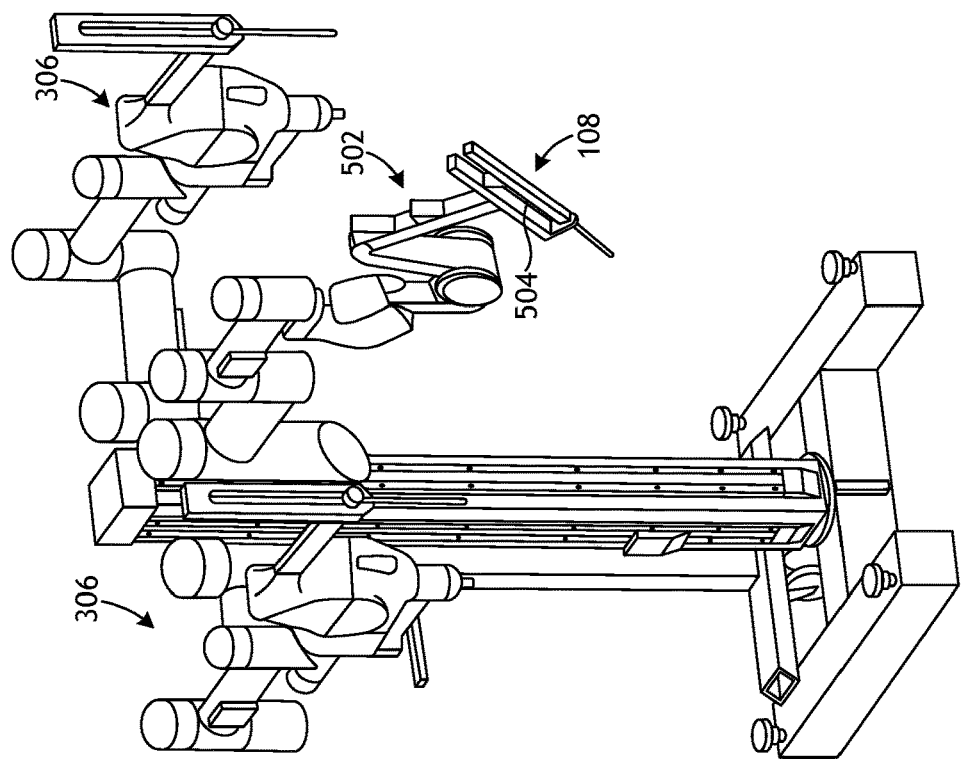
FIG. 5 is a perspective view of an alternative example robotic manipulator.

FIG. 5 is a perspective view of an alternative example robotic manipulator 502, used in conjunction with two robotic manipulators similar to the robotic manipulators 306 described in FIG. 4. As illustrated, a surgical tool 108 is mounted to a tool driver 504 supported by the robotic manipulator 502, which resides between two robotic manipulators 306 generally described above. Those of ordinary skill in the art will appreciate that various embodiments of the present invention may incorporate a wide variety of alternative robotic structures. Additionally, while the data communication between a robotic component and the processor of the robotic surgical system is primarily described herein with reference to communication between the surgical tool 108 and the master controller 102a (FIG. 2), it should be understood that similar communication may take place between circuitry of a robotic manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like.

Figure 6:
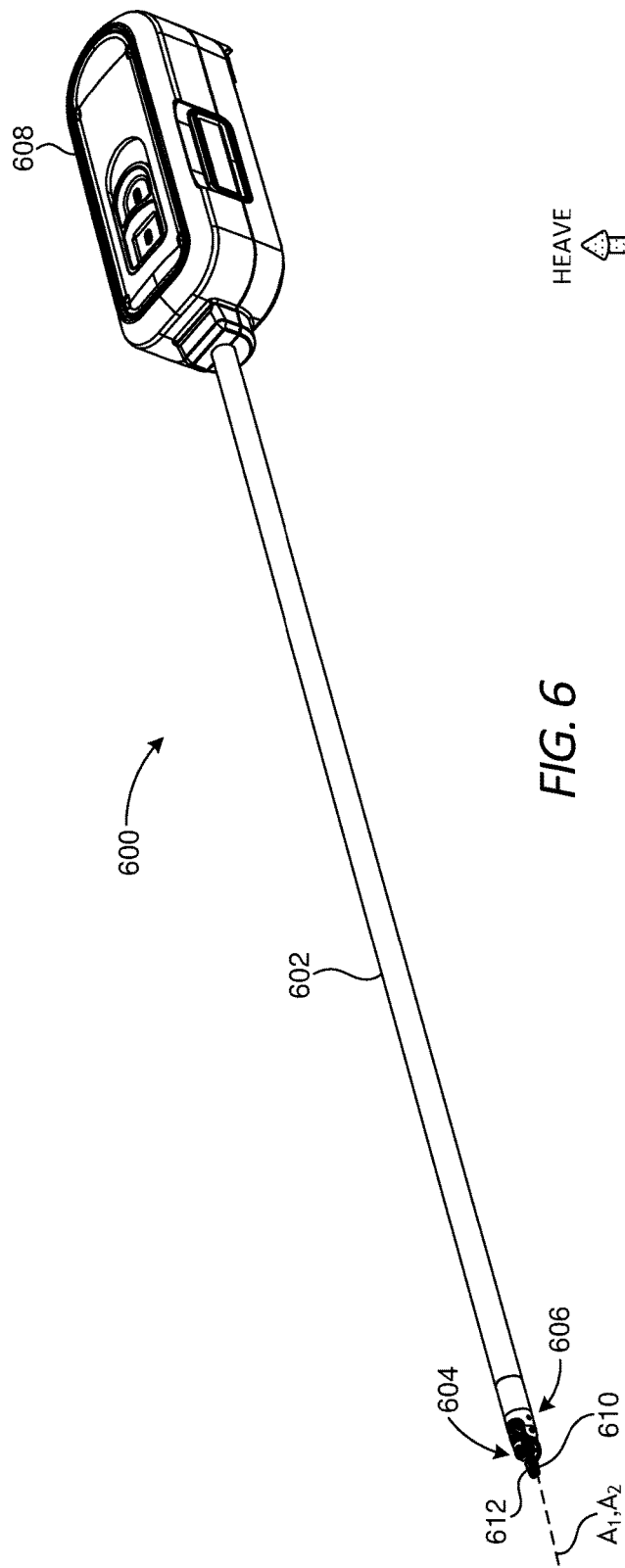
FIG. 6 is a side view of an example surgical tool that may incorporate some or all of the principles of the present disclosure.

FIG. 6 is side view of an example surgical tool 600 that may incorporate some or all of the principles of the present disclosure. The surgical tool 600 may be the same as or similar to the surgical tool(s) 108 of FIGS. 1 and 3-5 and, therefore, may be used in conjunction with a robotic surgical system, such as the robotic surgical system 100 of FIG. 1. Accordingly, the surgical tool 600 may be designed to be releasably coupled to a tool driver included in the robotic surgical system 100.

As illustrated, the surgical tool 600 includes an elongated shaft 602, an end effector 604, a wrist 606 (alternately referred to as a "wrist joint") that couples the end effector 604 to the distal end of the shaft 602, and a drive housing 608 coupled to the proximal end of the shaft 602. In applications where the surgical tool 600 is used in conjunction with a robotic surgical system (e.g., the robotic surgical system 100 of FIG. 1), the drive housing 608 can include coupling features that releasably couple the surgical tool 600 to the robotic surgical system. It will be appreciated, however, that the principles of the present disclosure are equally applicable to surgical tools that are non-robotic and otherwise capable of manual manipulation.

The terms "proximal" and "distal" are defined herein relative to a robotic surgical system having an interface configured to mechanically and electrically couple the surgical tool 600 (e.g., the housing 608) to a robotic manipulator. The term "proximal" refers to the position of an element closer to the robotic manipulator and the term "distal" refers to the position of an element closer to the end effector 604 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 600, the end effector 604 is configured to move (pivot) relative to the shaft 602 at the wrist 606 to position the end effector 604 at desired orientations and locations relative to a surgical site. To accomplish this, the housing 608 includes (contains) various drive inputs and mechanisms (e.g., gears, actuators, etc.) designed to control operation of various features associated with the end effector 604 (e.g., clamping, firing, rotation, articulation, energy delivery, etc.). In at least some embodiments, the shaft 602, and hence the end effector 604 coupled thereto, is configured to rotate about a longitudinal axis $A_1$ of the shaft 602. In such embodiments, at least one of the drive inputs included in the housing 608 is configured to control rotational movement of the shaft 602 about the longitudinal axis $A_1$.

The surgical tool 600 can have any of a variety of configurations capable of performing at least one surgical function. For example, the surgical tool 600 may include, but is not limited to, forceps, a grasper, a needle driver, scissors, an electro cautery tool, a stapler, a clip applier, a hook, a spatula, a suction tool, an irrigation tool, an imaging device (e.g., an endoscope or ultrasonic probe), or any combination thereof. In some embodiments, the surgical tool 600 may be configured to apply energy to tissue, such as radio frequency (RF) energy.

The shaft 602 extends distally from the housing 608 and has at least one lumen extending therethrough along its axial length. In some embodiments, the shaft 602 may be fixed to the housing 608, but could alternatively be rotatably mounted to the housing 608 to allow the shaft 602 to rotate about the longitudinal axis $A_1$. In yet other embodiments, the shaft 602 may be releasably coupled to the housing 608, which may allow a single housing 608 to be adaptable to various shafts having different end effectors.

The end effector 604 can have a variety of sizes, shapes, and configurations. In the illustrated embodiment, the end effector 604 comprises a tissue grasper that includes opposing jaws 610, 612 configured to move (articulate) between open and closed positions. As will be appreciated, however, the opposing jaws 610, 612 may alternatively form part of other types of end effectors such as, but not limited to, surgical scissors, a clip applier, a needle driver, a babcock including a pair of opposed grasping jaws, bipolar jaws (e.g., bipolar Maryland grasper, forceps, a fenestrated grasper, etc.), etc. One or both of the jaws 610, 612 may be configured to pivot to articulate the end effector 604 between the open and closed positions. It is noted, however, that the principles of the present disclosure are equally applicable to an end effector that does not include opposing jaws.

Figure 7:
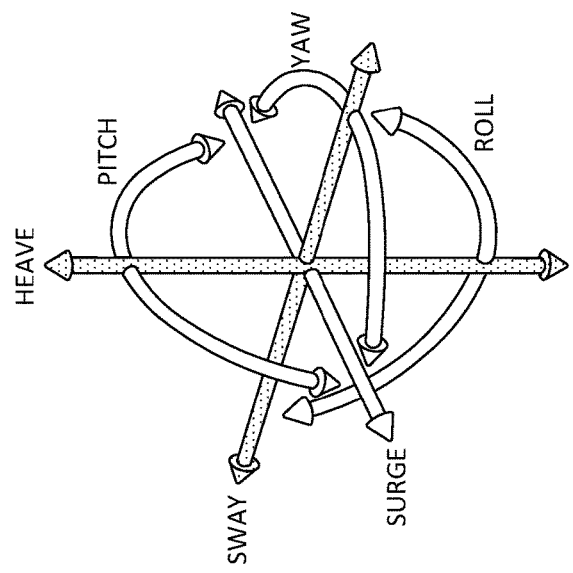
FIG. 7 illustrates potential degrees of freedom in which the wrist of FIG. 1 may be able to articulate (pivot).

FIG. 7 illustrates the potential degrees of freedom in which the wrist 606 may be able to articulate (pivot). The wrist 606 can have any of a variety of configurations. In general, the wrist 606 comprises a joint configured to allow pivoting movement of the end effector 604 relative to the shaft 602. The degrees of freedom of the wrist 606 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 604) with respect to a given reference Cartesian frame. As depicted in FIG. 7, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 606 (e.g., X-axis), yaw movement about a second axis of the wrist 606 (e.g., Y-axis), and combinations thereof to allow for 360° rotational movement of the end effector 604 about the wrist 606. In other applications, the pivoting motion can be limited to movement in a single plane, e.g., only pitch movement about the first axis of the wrist 606 or only yaw movement about the second axis of the wrist 606, such that the end effector 604 moves only in a single plane.

Referring again to FIG. 6, the surgical tool 600 may also include a plurality of drive cables (obscured in FIG. 6) that form part of a cable driven motion system configured to facilitate movement and articulation of the end effector 604 relative to the shaft 602. Moving (actuating) at least some of the drive cables moves the end effector 604 between an unarticulated position and an articulated position. The end effector 604 is depicted in FIG. 6 in the unarticulated position where a longitudinal axis $A_2$ of the end effector 604 is substantially aligned with the longitudinal axis $A_1$ of the shaft 602, such that the end effector 604 is at a substantially zero angle relative to the shaft 602. Due to factors such as manufacturing tolerance and precision of measurement devices, the end effector 604 may not be at a precise zero angle relative to the shaft 602 in the unarticulated position, but nevertheless be considered "substantially aligned" thereto. In the articulated position, the longitudinal axes $A_1$, $A_2$ would be angularly offset from each other such that the end effector 604 is at a non-zero angle relative to the shaft 602.

Figure 8:
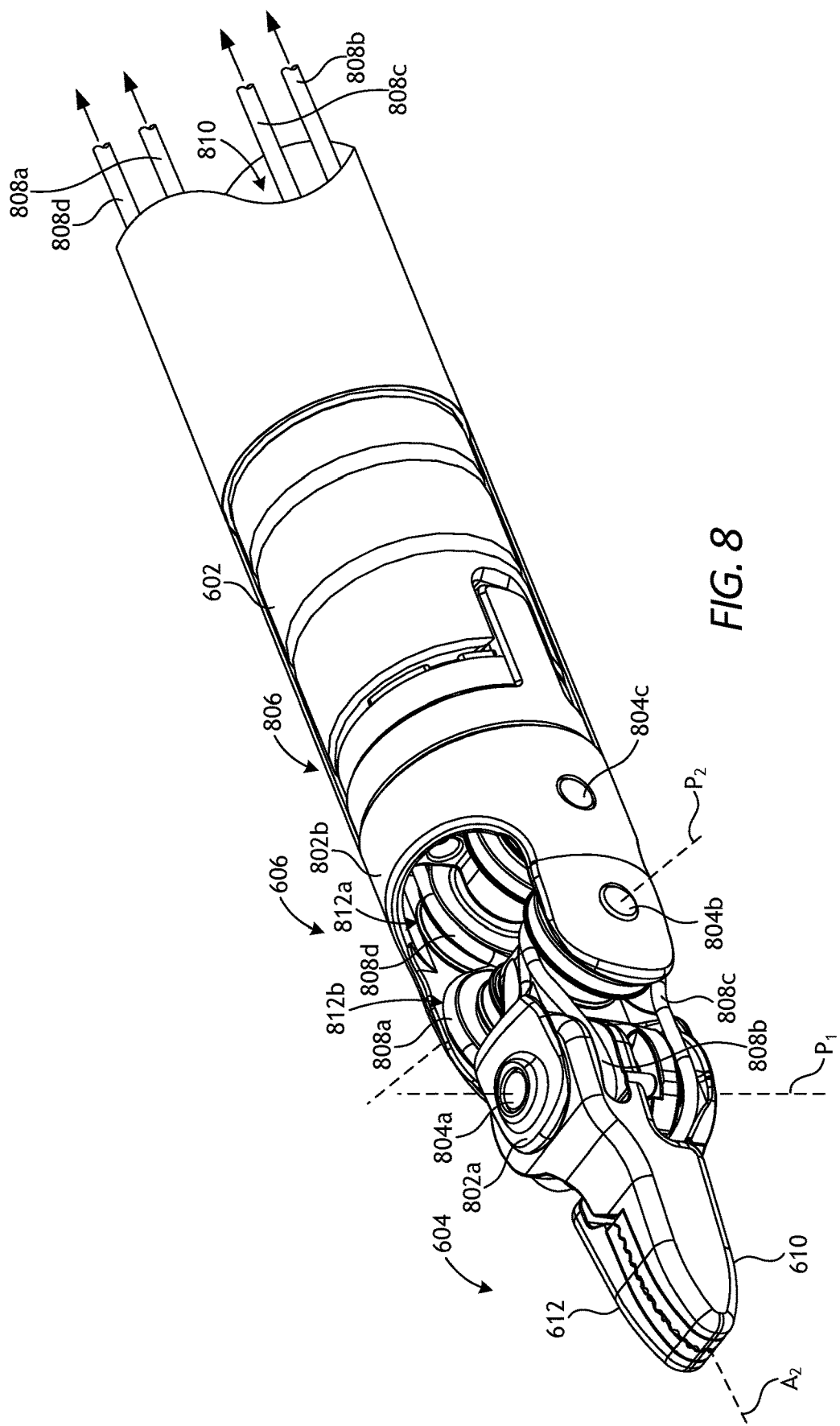
FIG. 8 is an enlarged isometric view of the distal end of the surgical tool of FIG. 1.

FIG. 8 is an enlarged isometric view of the distal end of the surgical tool 600 of FIG. 6. More specifically, FIG. 8 depicts enlarged views of the end effector 604 and the wrist 606, with the end effector 604 in the unarticulated position and the jaws 610, 612 closed. The wrist 606 operatively couples the end effector 604 to the shaft 602. To accomplish this, the wrist 606 includes a distal clevis 802a and a proximal clevis 802b. The jaws 610, 612 are rotatably mounted to the distal clevis 802a at a first axle 804a, the distal clevis 802a is rotatably mounted to the proximal clevis 802b at a second axle 804b, and the proximal clevis 802b is coupled to a distal end 806 of the shaft 602.

The wrist 606 provides a first pivot axis $P_1$ that extends through the first axle 804a and a second pivot axis $P_2$ that extends through the second axle 804b. The first pivot axis $P_1$ is substantially perpendicular (orthogonal) to the longitudinal axis $A_2$ of the end effector 604, and the second pivot axis $P_2$ is substantially perpendicular (orthogonal) to both the longitudinal axis $A_2$ and the first pivot axis $P_1$. Movement about the first pivot axis $P_1$ provides "yaw" articulation of the end effector 604, and movement about the second pivot axis $P_2$ provides "pitch" articulation of the end effector 604. In the illustrated embodiment, the jaws 610, 612 are mounted at the first pivot axis $P_1$, thereby allowing the jaws 610, 612 to pivot relative to each other to open and close the end effector 604 or alternatively pivot in tandem to articulate the orientation of the end effector 604.

A plurality of drive cables, shown as drive cables 808a, 808b, 808c, and 808d, extend longitudinally within a lumen 810 defined by the shaft 602 and pass through the wrist 606 to be operatively coupled to the end effector 604. The lumen 810 can be a single lumen, as illustrated, or can alternatively comprise a plurality of independent lumens, where each lumen receives one or more of the drive cables 808a-d.

The drive cables 808a-d form part of the cable driven motion system briefly described above, and may be referred to and otherwise characterized as cables, bands, lines, cords, wires, ropes, strings, twisted strings, elongate members, etc. The drive cables 808a-d can be made from a variety of materials including, but not limited to, metal (e.g., tungsten, stainless steel, etc.) or a polymer. While four drive cables 808a-d are depicted in FIG. 8, more or less than four drive cables 808a-d may be included, without departing from the scope of the disclosure.

The drive cables 808a-d extend proximally from the end effector 604 to the drive housing 608 (FIG. 6) where they are operatively coupled to various actuation mechanisms or devices housed (contained) therein to facilitate longitudinal movement (translation) of the drive cables 808a-d within the lumen 810. Selective actuation of all or a portion of the drive cables 808a-d causes the end effector 604 to articulate (pivot) relative to the shaft 602. More specifically, selective actuation causes a corresponding drive cable 808a-d to translate longitudinally within the lumen 810 and thereby cause pivoting movement of the end effector 604. One or more drive cables 808a-d, for example, may be actuated to cause the end effector 604 to articulate (e.g., both of the jaws 610, 612 angled in a same direction), to cause the end effector 604 to open (e.g., one or both of the jaws 610, 612 move away from the other), or to cause the end effector 604 to close (e.g., one or both of the jaws 610, 612 move toward the other).

Moving the drive cables 808a-d can be accomplished in a variety of ways, such as by triggering an associated actuator or mechanism operatively coupled to or housed within the drive housing 608 (FIG. 6). Moving a given drive cable 808a-d constitutes applying tension (i.e., pull force) to the given drive cable 808a-d in a proximal direction, which causes the given drive cable 808a-d to translate and thereby cause the end effector 604 to move (articulate) relative to the shaft 602.

The wrist 606 includes a first set of pulleys 812a and a second set of pulleys 812b, each configured to interact with and redirect the drive cables 808a-d for engagement with the end effector 604. The first set of pulleys 812a is mounted to the proximal clevis 802b at the second axle 804b and the second set of pulleys 812b is also mounted to the proximal clevis 802b but at a third axle 804c located proximal to the second axle 804b. The first and second sets of pulleys 812a,b cooperatively redirect the drive cables 808a-d through an "S" shaped pathway (alternately referred to as an "S-curve" or "S-bend") before the drive cables 808a-d are operatively coupled to the end effector 604.

In at least one embodiment, one pair of drive cables 808a-d is operatively coupled to each jaw 610, 612 and configured to "antagonistically" operate the corresponding jaw 610, 612. In the illustrated embodiment, for example, the first and second drive cables 808a,b may be coupled at the first jaw 610, and the third and fourth drive cables 808c,d may be coupled at the second jaw 612. Actuation of the first drive cable 808a acts on and pivots the first jaw 610 about the first pivot axis $P_1$ toward the open position. In contrast, actuation of the second drive cable 808b acts on and pivots the first jaw 610 about the first pivot axis $P_1$ toward the closed position. Similarly, actuation of the third drive cable 808c pivots the second jaw 612 about the first pivot axis $P_1$ toward the open position, while actuation of the fourth drive cable 808d pivots the second jaw 612 about the first pivot axis $P_1$ toward the closed position.

Accordingly, the drive cables 808a-d may be characterized or otherwise referred to as "antagonistic" cables that cooperatively (yet antagonistically) operate to cause relative or tandem movement of the first and second jaws 610, 612. When the first drive cable 808a is actuated (moved), the second drive cable 808b naturally follows as coupled to the first drive cable 808a, and vice versa. Similarly, when the third drive cable 808c is actuated, the fourth drive cable 808d naturally follows as coupled to the third drive cable 808c, and vice versa.

Moreover, coordinated actuation of the drive cables 808a-d may also articulate the end effector 604 about the second pivot axis $P_2$. Consequently, the end effector 604 can articulate with multiple degrees of freedom, e.g., a degree of freedom by articulating about the first pivot axis $P_1$ and another degree of freedom by articulating about the second pivot axis $P_2$. The wrist 606 in this embodiment is pivotable about the second pivot axis $P_2$ in a single plane, e.g., in one of pitch and yaw, and the end effector 604 is pivotable about the first pivot axis $P_1$ in a single, different plane, e.g., the other of pitch and yaw.

Figure 9:
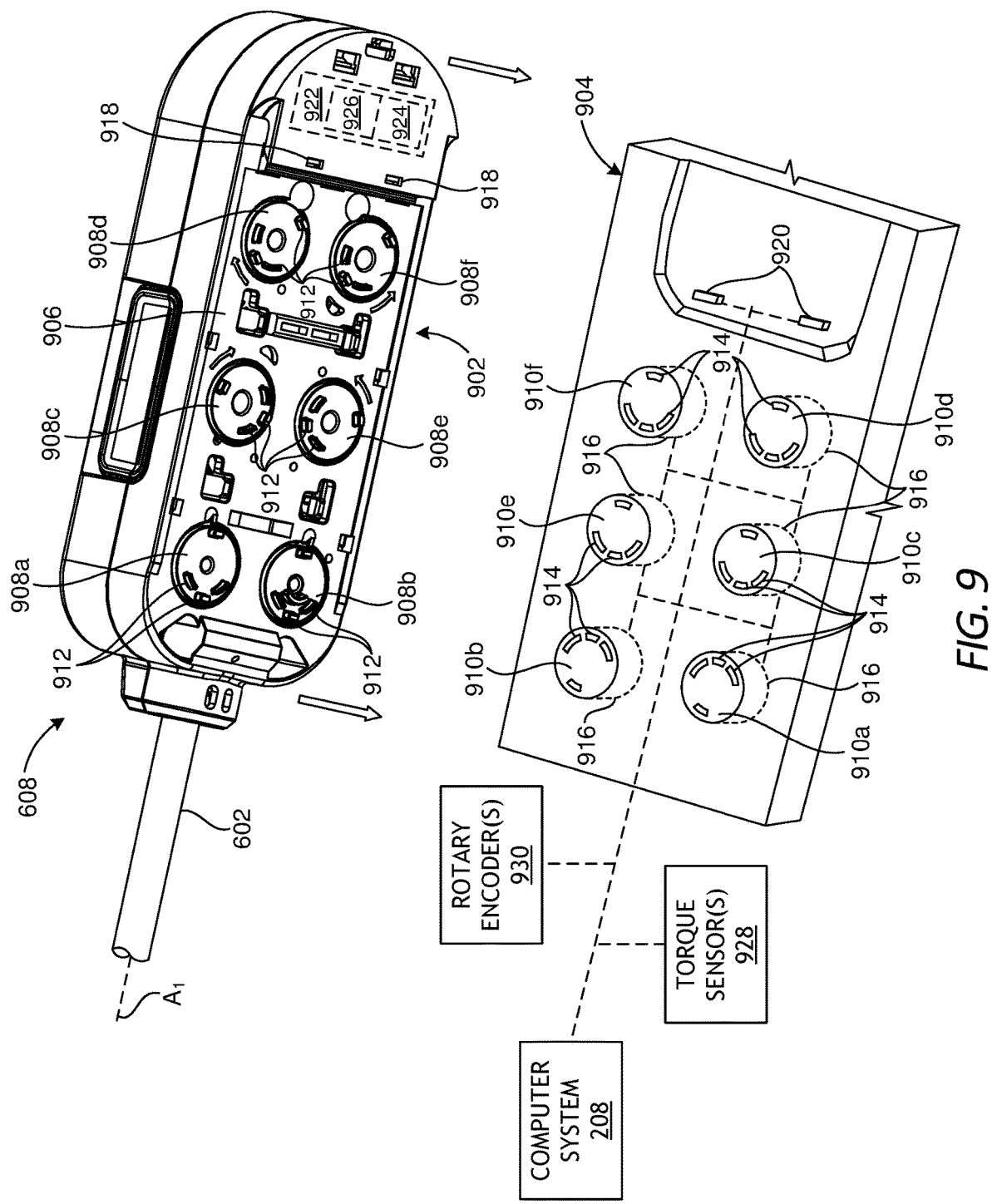
FIG. 9 is a bottom view of the drive housing of the surgical tool of FIG. 6.

FIG. 9 depicts a bottom view of the drive housing 608, according to one or more embodiments. As illustrated, the drive housing 608 (alternately referred to as a "puck") may include a tool mounting portion 902 used to operatively couple the drive housing 608 to a tool driver 904. The tool driver 904 may be the same as or similar to any of the tool drivers mentioned herein (e.g., the tool drivers 308, 504 of FIGS. 3 and 5, respectively), and may thus be operable in conjunction with any of the robotic manipulators also mentioned herein (e.g., the robotic manipulators 306, 502 of FIGS. 3 and 5, respectively). Accordingly, mounting the drive housing 608 to the tool driver 904 may place the drive housing 608 in communication with the computer system 208 of the master controller 102a (FIG. 1), thus allowing the computer system 208 to monitor and facilitate operation of the drive housing 608.

The tool mounting portion 902 includes and otherwise provides an interface 906 that mechanically, magnetically, and/or electrically couples the drive housing 608 to the tool driver 904. As illustrated, the interface 906 includes and supports a plurality of inputs, shown as drive inputs 908a, 908b, 908c, 908d, 908e, and 908f. Each drive input 908a-f may comprise a rotatable disc configured to align with and couple to a corresponding driver 910a, 910b, 910c, 910d, 910e, and 910f of the tool driver 904. Moreover, each drive input 908a-f and corresponding driver 910a-f provide or define one or more surface features 912 and 914, respectively, configured to align and mate to facilitate mating engagement between the opposing structures such that movement of a given driver 910a-f correspondingly moves the associated drive input 908a-f.

Each driver 910a-f may include or otherwise comprise a motor 916 configured to actuate the corresponding driver 910a-f. Each motor 916 may be in communication with the computer system 208 and, based on input signals provided by a user (e.g., a surgeon), the computer system 208 may selectively cause any of the motors 916 to actuate and thereby drive the corresponding driver 910a-f. When the drive housing 608 is properly mounted to the tool driver 904, actuation of a given driver 910a-f will correspondingly cause actuation of the mated drive input 908a-f. In the illustrated embodiment, actuation of the motors 916 causes rotational movement of the corresponding driver 910a-f, which, in turn, rotates the associated drive input 908a-f. In other embodiments, however, one or more of the motors 916 may be designed to actuate the corresponding driver 910a-f via other mechanical movements, such as lateral movement (e.g., side-to-side translation), axial movement (e.g., up and down) translation, etc., without departing from the scope of the disclosure.

In some embodiments, actuation of the first drive input 908a via the first driver 910a may control rotation of the elongate shaft 602 about its longitudinal axis $A_1$. The elongate shaft 602 may be rotated clockwise or counter-clockwise depending on the rotational actuation of the first drive input 908a. Actuation of the second drive input 908b via the second driver 910b may control a lockout mechanism (alternately referred to as a deadbolt) designed to lock the end effector 604 (FIGS. 6 and 8) in a predetermined pose or position. Actuation of the third, fourth, fifth, and sixth drive inputs 908c-f via the third, fourth, fifth, and sixth drivers 910a-f, respectively, may cause movement (axial translation) of the associated drive cables 808a-d (FIG. 8), respectively, which results in the articulation of the end effector 604 (FIGS. 6 and 8).

In some embodiments, the drive housing 608 may also be electrically coupled to the tool driver 904. In such embodiments, the interface 906 may further include one or more electrical connection points 918 (two shown) configured to mate with corresponding electrical connections 920 (two shown) provided by the tool driver 904. Alternately, the drive housing 608 can be coupled wirelessly (e.g., near field communication). Moreover, the drive housing 608 may further house or otherwise include an internal computer 922 that may include a memory 924 and/or a microprocessor 926. The memory 924 may include one or more databases or libraries that store data relating to the drive housing 608 and, more particularly, to the surgical tool 600. Mating the connection points 918 with the electrical connections 920 may place the internal computer 922 in communication with the computer system 208 via the tool driver 904.

According to embodiments of the present disclosure, the computer system 208 may be configured and otherwise programmed to monitor, store, and/or report operational usage of the surgical tool 600 (FIG. 6). Each surgical tool has a useful lifespan during which the tool will generally operate as expected without risk of mechanical failure. Over prolonged usage, however, the operational integrity of the surgical tool can diminish, thus increasing the probability of failure. In the present scenario, the drive cables 808a-d (FIG. 8) of the surgical tool 600 are repeatedly subjected to applied loading and unloading during operation that, over time, can weaken the cable material and cause fatigue. To avoid inefficient operation of the surgical tool 600, and/or prevent failure of one or more of the drive cables 808a-d mid-operation, the computer system 208 may be programmed and otherwise configured to monitor usage of the drive cables 808a-d and provide operational feedback as needed.

Figure 10:
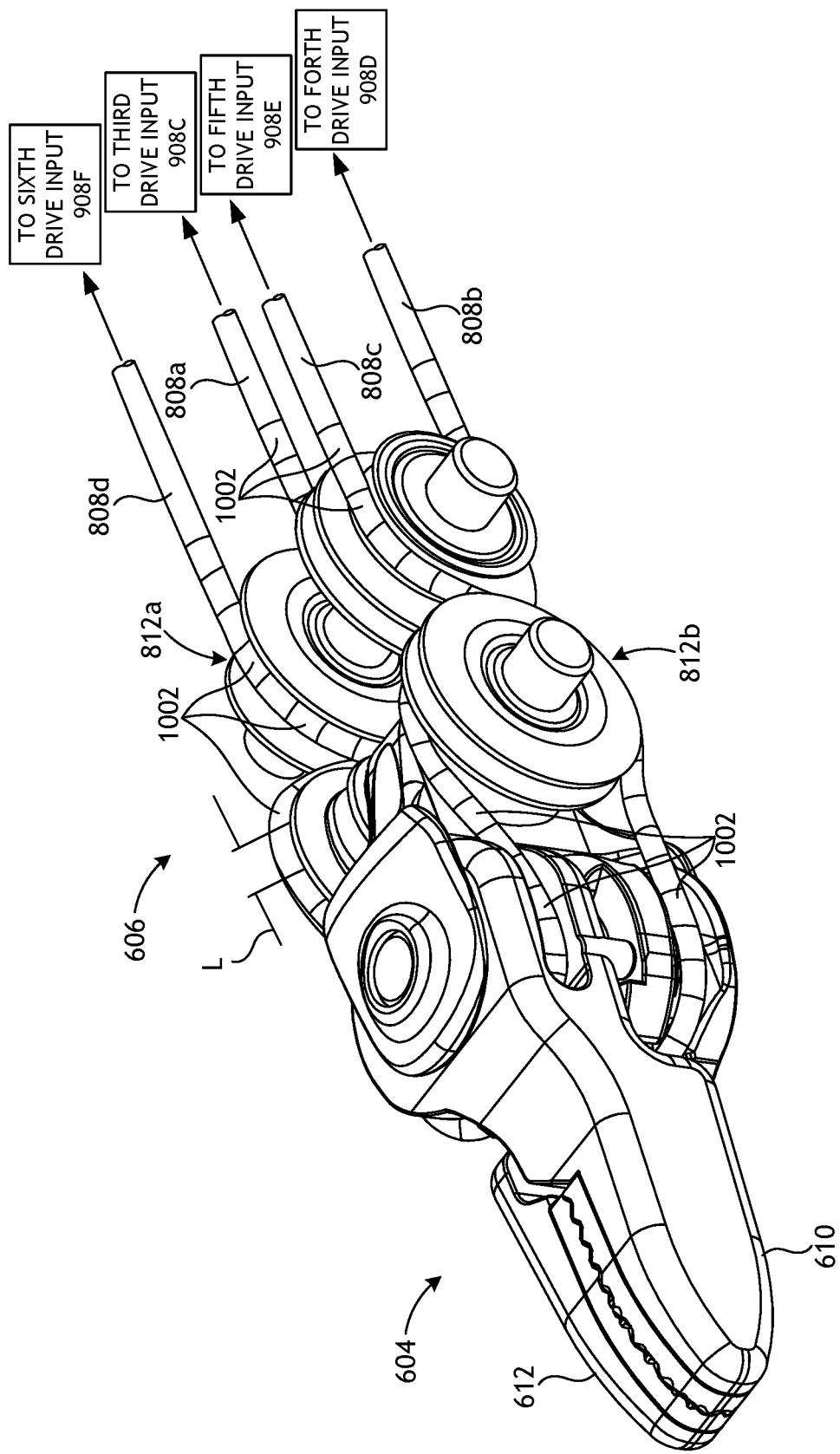
FIG. 10 is an enlarged isometric view of the end effector and the wrist of FIG. 8.

FIG. 10 is an enlarged isometric view of the end effector 604 and the wrist 606 of FIG. 8. The proximal clevis 802b (FIG. 8) and the shaft 602 (FIG. 8) are omitted in FIG. 10 to enable viewing of the internal parts of the wrist 606. As illustrated, the drive cables 808a-d extend proximally from the end effector 604 to corresponding drive inputs 908c-f. At the wrist 606, the drive cables 808a-d are redirected and otherwise routed through the first and second sets of pulleys 812a and 812b. The path taken by each drive cable 808a-d through the pulleys 812a,b results in each drive cable 808a-d extending through an S-bend, or "S" shaped pathway.

During operation of the end effector 604, the drive cables 808a-d may be subjected to constant tensile loading originating at the corresponding drive inputs 908c-f. Such tensile loading, over time, introduces fatigue in the cable material, which can diminish efficiency of the drive cables 808a-d. Moreover, as the drive cables 808a-d are actuated, additional tensile loading can be introduced as the jaws 610, 612 grasp objects and tensile strain is applied to the drive cables 808a-d to maintain the grip. Furthermore, as the drive cables 808a-d are actuated, portions of the drive cables 808a-d are progressively moved (translated) through the S-bend defined by the pulleys 812a,b, which further subjects the drive cables 808a-d to opposing bending loads that introduce additional fatigue in the material of the drive cables 808a-d.

According to one or more embodiments, a plurality of discrete segments 1002 may be defined or otherwise identified along all or a portion of each drive cable 808a-d. The segments 1002 may be contiguous (consecutive) along the respective drive cables 808a-d, and the exact location of each segment 1002 relative to the end effector 604 (or another known point in the surgical tool 600) may be known (determined) at any time by calculating the distance from the corresponding drive input 908c-f. When a given drive input 908c-f is actuated to move the associated drive cable 808a-d, the dynamic location of each segment 1002 along the associated drive cable 808a-d can be determined, tracked, and recorded. As discussed below, this may be accomplished through the use of one or more rotational position encoders (e.g., rotary encoders 930 of FIG. 9) most likely located adjacent to each motor 916.

While the segments 1002 are depicted in FIG. 10 as being located near the distal ends of the drive cables 808*a-d*, the segments 1002 may alternatively be defined along the entire length of the drive cables 808*a-d*, without departing from the scope of the disclosure. Each segment 1002 may exhibit a predetermined and known length L. The length L of each segment 1002 may vary depending on the application, and may or may not be the same as axially adjacent segments 1002 in the same drive cable 808*a-d* or otherwise on other drive cables 808*a-d*. However, the length L and real-time location of each segment 1002 may be known such that accurate positional tracking of each segment 1002 may be determined. In some embodiments, the length L of a given segment 1002 may range between about 0.001 inches and about 4.0 inches. As will be appreciated, however, the length L may alternatively be less than 0.001 inches or greater than 4.0 inches, without departing from the scope of the disclosure.

Referring again to FIG. 9, with continued reference to FIG. 10, to help monitor operational usage of the drive cables 808*a-d*, each segment 1002 of each drive cable 808*a,b* may exhibit or otherwise be provided with a usage value corresponding to the lifetime operational usage of the corresponding segment 1002. Accordingly, the current usage value for a given segment 1002 corresponds to the amount and magnitude of usage the segment 1002 has undergone throughout its operational life. Current usage value may be determined at any time based on the past and present operational usage of the given segment 1002.

In some embodiments, current usage values for all segments 1002 may be stored in the internal computer 922 (e.g., the memory 924) of the drive housing 608. Consequently, whenever the drive housing 608 is mounted to a tool driver, such as the tool driver 904, the usage values may be accessible by the computer system 208 for processing. In other embodiments, the usage values for the segments 1002 may be stored in the memory of the computer system 208. In such embodiments, once the drive housing 608 is mounted to a tool driver, such as the tool driver 904, the computer system 208 may recognize the surgical tool 600 (FIG. 6) and access current usage values of each segment 1002 from a local memory of the computer system 208. In yet other embodiments, the current usage values for all segments 1002 may be stored remotely, such as in a removable computer-readable medium (e.g., a removable disk, a flash drive, a CD-ROM, a DVD, etc.). Alternatively, the current usage values for all segments 1002 may be remotely stored in the Cloud and may be retrieved via suitable wired or wireless means when needed.

According to the present disclosure, the computer system 208 may be programmed and otherwise configured to alter the usage value of a given segment 1002 based on usage of the surgical tool 600 (FIG. 6) and, more particularly, based on operational movement (translation) of the drive cable 808*a-d* associated with the given segment 1002. In some embodiments, for example, one or more torque sensors 928 may be used to measure the real-time tensile loading assumed by each drive cable 808*a-d* at any given moment. The torque sensor(s) 928 may be communicably coupled to the computer system 208 to provide continuous (or intermittent) tension data for each drive cable 808*a-d* during operation. In some embodiments, individual torque sensors 928 may be operatively coupled to each driver 910*c-f*, but may alternatively be operatively coupled to each drive input 908*c-f*. In either scenario, the torque sensors 928 may be able to communicate with the internal computer 922 of the drive housing 608, which may be able to communicate with the computer system 208 to provide real-time tensile data for processing.

The tensile loading assumed by each drive cable 808*a-d*, as measured by the corresponding torque sensor 928, may be applied to increase the usage value of each segment 1002 affected by the torque loading. In some embodiments, the usage value may be increased by a preset number or value each time tensile loading is experienced by a given segment 1002. In other embodiments, the usage value may be calculated as a magnitude that may be proportional to the magnitude of the tensile loading assumed by the given segment 1002. More particularly, the computer system 208 may be programmed to increase the usage value of each affected segment 1002 by an amount commensurate with the magnitude of the torque loading. In some embodiments, tensile loads assumed by the given segment 1002 below a predefined threshold may not increase the usage value.

The computer system 208 may communicate with the torque sensors 928 in real-time to receive torque loading measurements and calculate the resulting tensile loading on the affected drive cables 808*a-d*. This may be done for all operations of the surgical tool 600 (FIG. 6) that result in tensile loading on the drive cables 808*a-d*, including, but not limited to, articulation of the end effector 204, opening and closing the jaws 610, 612, grasping onto objects (e.g., tissue) with the jaws 610, 612, etc. During operation in real-time or otherwise following a procedure or operation of the surgical tool 600, the computer system 208 may aggregate the usage value increments to determine the current (real-time) usage value of each segment 1002.

To further help monitor operational usage of the drive cables 808*a-d*, one or more rotary encoders 930 may be used to measure the rotational output of each driver 910*c-f*, which may help determine the location of each segment 1002 along the length of the associated drive cables 808*a-d*. The rotary encoder(s) 930 may be communicably coupled to the computer system 208 to provide continuous (or intermittent) location data for each drive cable 808*a-d* during operation. In some embodiments, individual rotary encoders 930 may be operatively coupled to each driver 910*c-f*, but may alternatively be operatively coupled to each drive input 908*c-f*. In either scenario, the rotary encoders 930 may communicate with the computer system 208 to provide real-time rotational output data for each drive input 908*c-f* or each driver 910*c-d*, which may be processed by the computer system 208 to determine the linear distance traveled by each segment 1002 of the associated drive cable 808*a-d*.

In example operation, if the rotary encoder 930 monitoring rotation of a given driver 910*c-f* (or drive input 908*c-f*) measures a rotation of 30°, the computer system 208 may be programmed to determine the corresponding linear distance that a given segment 1002 of the associated drive cable 808*a-d* may traverse proportional to the 30° rotation. The calculated linear distance may then be applied to determine if the given segment 1002 has traversed (partially or fully) the S-bend defined by the pulleys 812*a,b*. If the given segment 1002 traverses the S-bend (even partially), the usage value of the given segment 1002 may be correspondingly increased since traversing the S-bend will subject the segment 1002 bending loads that introduce fatigue in the material of the associated drive cable 808*a-d*.

More specifically, in some embodiments, linear translation of the given segment 1002 caused by rotation of an associated driver 910*c-f* (or drive input 908*c-f*) may result in the given segment 1002 undergoing a full bending reversal through the S-bend. As used herein, "full bending reversal"

refers to the segment 1002 fully traversing both pulleys 812*a,b* and thereby assuming bending on both sides (inner and outer portions) of the segment 1002. In other embodiments, linear translation of the given segment 1002 may result in the segment 1002 undergoing partial bending reversal through the S-bend. As used herein, "partial bending reversal" refers to the segment 1002 traversing only one (or a portion of one) of the pulleys 812*a,b* and thereby assuming bending on only one side (inner or outer portion) of the segment 1002.

In some embodiments, the usage value of the segment 1002 may be increased by corresponding preset numbers or values each time the segment 1002 undergoes a full bending reversal or a partial bending reversal. In such embodiments, the usage value increment corresponding to the segment 1002 undergoing a full bending reversal would be larger than the usage value increment corresponding to the segment 1002 undergoing a partial bending reversal.

In other embodiments, however, the usage value may be calculated as a magnitude of the bending forces assumed by the segment 1002 as a result of linearly traversing the S-bend provided by the pulleys 812*a,b*. In such embodiments, data obtained from the torque sensors 928 and the rotary encoders 930 may be combined to determine the magnitude of the usage value increase. More specifically, the computer system 208 may first be configured to determine whether the segment 1002 underwent full bending reversal or partial bending reversal. As described above, this can be determined from the rotational output data obtained by the corresponding rotary encoder 930, which may be translated into a linear distance traveled by the given segment 1002. The linear distance calculation may then be combined with the tensile loading assumed by the segment 1002 as measured by the torque sensor(s) 928 during such movement.

The computer system 208 may communicate with the torque sensors 928 and the rotary encoders 930 in real-time to calculate the resulting usage value increase on the affected drive cables 808*a-d*. This may be done for all operations of the surgical tool 600 (FIG. 6) that result in tensile loading on the drive cables 808*a-d* as they traverse the S-bend. During operation in real-time or otherwise following a procedure or operation of the surgical tool 600, the computer system 208 may aggregate the usage value increments to determine the current (real-time) usage value of each segment 1002.

In some embodiments, the computer system 208 may be configured to apply a cumulative damage model that aggregates the usage value increments of each segment 1002 over time to provide a real-time (current) usage value. In some embodiments, for example, the computer system 208 may be programmed to apply Miner's Rule, and thereby calculate damage caused by cyclic/frequency and magnitude variant loading during operation of the surgical tool 600 (FIG. 6). Usage values may continue to increment (increase) from the usage values calculated at the end of the previous procedure or operation.

In some embodiments, the computer system 208 may be programmed or otherwise configured to preemptively predict when a given drive cable 808*a-d* might fail based on the accumulated and current usage value of one or more associated segments 1002. Each drive cable 808*a-d* may have a predetermined failure limit that may be provided, for example, by a manufacturer. As the usage values for specific segments 1002 of a given drive cable 808*a-d* approach the predetermined failure limit, the computer system 208 may be configured to calculate and prognosticate the remaining useful life of the drive cable 808*a-d*, which may be accessible by a user (e.g., a surgeon or clinician), or may be transmitted to the user as an alert. Consequently, the user may be apprised of a general timeline or time frame when the drive cable 808*a-d* may need to be retired or replaced.

Once a predetermined usage value is reached for any segment 1002 of any drive cable 808*a-d*, the computer system 208 may be programmed to provide or issue an alert. In some embodiments, the predetermined usage value may correspond to the predetermined failure limit reached by a given drive cable 808*a-d*. In other embodiments, the predetermined usage value may correspond to a percentage of the predetermined failure limit reached by the given drive cable 808*a-d*. In such embodiments, the alert issued to the user may indicate that a specific percentage (e.g., 75%, 90%, 95%, 99%, etc.) of the predetermined failure limit has been reached.

The alerts mentioned herein may take many forms including, but not limited to, an audible alert, a visual alert, an electronic alert (e.g., email, text message, etc.), a vibratory alert (e.g., issued through the physical controllers held by the operator), or any combination thereof. In at least one embodiment, visual alerts may be sent to the stereo display 204 (FIG. 2) and/or the feedback meter 206 (FIG. 1) viewable by a user during operation.

In some embodiments, the alerts may become more severe (intense) as the usage value approaches the predetermined failure limit for a given drive cable 808*a-d*. For example, a mild alert may be issued when the usage value for a specific segment 1002 reaches 75% of the predetermined failure limit for the given drive cable 808*a-d*. A more severe (e.g., louder, brighter, more forceful vibration, etc.) alert may be issued when the usage value for the specific segment 1002 reaches a larger percentage, such as 90% or higher. An even more severe alert may be issued when the usage value for the specific segment 1002 reaches 100% of the predetermined failure limit.

In some embodiments, once a predetermined usage value is reached for any segment 1002 of any drive cable 808*a-d*, the computer system 208 may be programmed to prevent the surgical tool 600 (FIG. 6) from further operation or otherwise being used in a subsequent procedure. In such embodiments, the predetermined usage value may comprise the predetermined failure limit for a given drive cable 808*a-d*. In at least one embodiment, however, the predetermined usage value may include an operational margin below the predetermined failure limit that allows the surgical tool 600 to continue to be used to finish the current procedure. Following that procedure, however, the surgical tool 600 may be prevented from being used in a subsequent procedure.

Once a given drive cable 808*a-d* reaches the predetermined usage value and the surgical tool 600 (FIG. 6) is prevented from participating in further procedures, the surgical tool 600 may be disabled to prevent its use in any future procedures. In at least one embodiment, the surgical tool 600 may be retired (e.g., scrapped). In other embodiments, however, the surgical tool 600 may alternatively be refurbished. In such embodiments, the surgical tool 600 may be dismantled and the drive cables 808*a-d* may be replaced. In some embodiments, however, only the drive cable(s) 808*a-d* that reached the predetermined usage value may be replaced. Accordingly, monitoring and reporting usage values for individual segments 1002 on each drive cable 808*a-d* may prove advantageous in not requiring a complete overhaul of the surgical tool 600 upon one drive cable 808*a-d* reaching the predetermined usage value. Rather, only the affected drive cable 808*a-d* need be replaced. As will be appreciated, this may extend the life of the surgical tool 600 by not prematurely or unnecessarily replacing component parts.

In some embodiments, the usage value of the segments 1002 may be increased as a result of non-operational procedures or "life events." For example, the usage value of the segments 1002 may be increased following an autoclave cycle where elevated cycling of pressure and temperature can adversely affect the material properties of the drive cables 808a-d. The usage value of the segments 1002 may also be increased based on the amount of time the drive housing 608 is mounted to the tool driver 904, since mounting the drive housing 608 to the tool driver 904 places the drive cables 808a-d in constant tension that might adversely affect the material properties of the drive cables 808a-d over time. The usage value of the segments 1002 may further be increased based on the number of times the drive housing 608 is mounted and detached from a tool driver. More specifically, mounting and detaching the drive housing 608 to/from the drive housing 904 subjects the drive cables 808a-d to tensile loading and unloading, which can, over time, adversely affect the material properties of the drive cables 808a-d.

In some embodiments, the computer system 208 may be programmed and otherwise configured to increase the usage value of the segments 1002 based on the number of procedures undertaken by the surgical tool 600 (FIG. 6). In such embodiments, regardless of whether the drive cables 808a-d are actually used in a particular procedure, the computer system 208 may nonetheless increase the usage value of each segment 1002 of each drive cable 808a-d included in the surgical tool 600.

As will be appreciated, the principles of the present disclosure may be expanded to general usage of a surgical tool itself. More specifically, the computer system 208 may be programmed or otherwise configured to track the number of times the surgical tool 600 (FIG. 6) is coupled to the tool driver 904 (or any tool driver) and used in a surgical procedure. The surgical tool 600 may have a predetermined procedure limit, and each time the surgical tool 600 is used in a surgical procedure, the computer system 208 registers a usage value, regardless of whether the surgical tool 600 was actually used in the procedure or not. Once the usage value reaches the predetermined procedure limit, the surgical tool 600 may be prevented from being used in any future surgical procedures but may instead be retired or refurbished.

The systems, devices, and methods disclosed herein can be implemented using the computer system 208, which may also be referred to herein as digital data processing systems and programmable systems. One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and programmable logic devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 11:
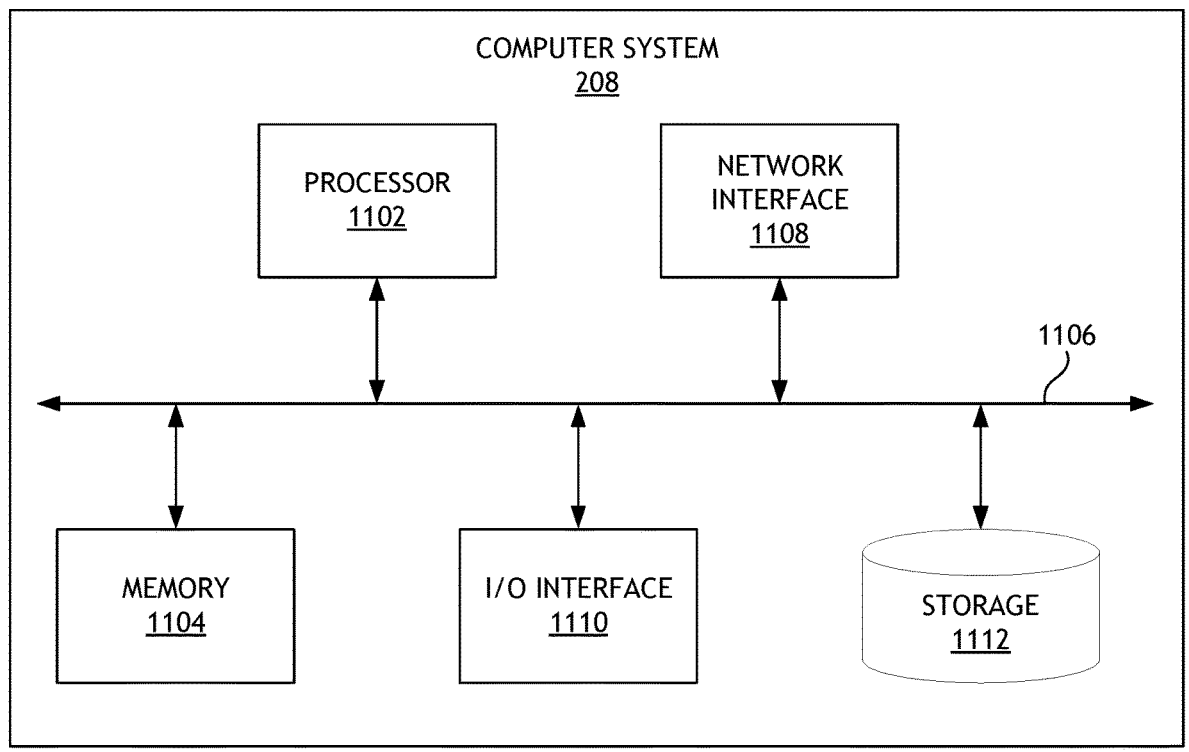
FIG. 11 illustrates one example embodiment of the computer system of FIGS. 2 and 9.

FIG. 11 illustrates an example embodiment of the computer system 208. As shown, the computer system 208 includes one or more processors 1102, which can control the operation of the computer system 208. "Processors" are also referred to herein as "controllers." The processor(s) 1102 can include any type of microprocessor or central processing unit (CPU), including programmable general-purpose or special-purpose microprocessors and/or any one of a variety of proprietary or commercially available single or multi-processor systems. The computer system 208 can also include one or more memories 1104, which can provide temporary storage for code to be executed by the processor(s) 1102 or for data acquired from one or more users, storage devices, and/or databases. The memory 1104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 208 can be coupled to a bus system 1106. The illustrated bus system 1106 is an abstraction that represents any one or more separate physical busses, communication lines/interfaces, and/or multi-drop or point-to-point connections, connected by appropriate bridges, adapters, and/or controllers. The computer system 208 can also include one or more network interface(s) 1108, one or more input/output (IO) interface(s) 1110, and one or more storage device(s) 1112.

The network interface(s) 1108 can enable the computer system 208 to communicate with remote devices, e.g., other computer systems, over a network, and can be, for non-limiting example, remote desktop connection interfaces, Ethernet adapters, and/or other local area network (LAN) adapters. The IO interface(s) 1110 can include one or more interface components to connect the computer system 208 with other electronic equipment. For non-limiting example, the IO interface(s) 1110 can include high speed data ports, such as universal serial bus (USB) ports, 1394 ports, Wi-Fi, Bluetooth, etc. Additionally, the computer system 208 can be accessible to a human user, and thus the IO interface(s) 1110 can include displays, speakers, keyboards, pointing devices, and/or various other video, audio, or alphanumeric interfaces. The storage device(s) 1112 can include any conventional medium for storing data in a non-volatile and/or non-transient manner. The storage device(s) 1112 can thus hold data and/or instructions in a persistent state, i.e., the value(s) are retained despite interruption of power to the computer system 208. The storage device(s) 1112 can include one or more hard disk drives, flash drives, USB drives, optical drives, various media cards, diskettes, compact discs, and/or any combination thereof and can be directly connected to the computer system 208 or remotely connected thereto, such as over a network. In an exemplary embodiment, the storage device(s) 1112 can include a tangible or non-transitory computer readable medium configured to store data, e.g., a hard disk drive, a flash drive, a USB drive, an optical drive, a media card, a diskette, a compact disc, etc.

The elements illustrated in FIG. 11 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 208 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 208 can also include a web server for generating and/or delivering the web pages to client computer systems.

In an exemplary embodiment, the computer system 208 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

The computer system 208 can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Embodiments disclosed herein include:

A. A method of operating a surgical tool may include mounting the surgical tool to a tool driver, the surgical tool including one or more drive cables movable to actuate an end effector, wherein one or more segments are defined along a portion of at least one of the one or more drive cables and each segment exhibits a usage value, monitoring usage of the one or more drive cables with a computer system in communication with the tool driver, and altering the usage value of at least one of the one or more segments based on usage of the surgical tool.

B. A non-transitory medium readable by a processor and storing instructions for execution by the processor for performing a method that may include monitoring usage of one or more drive cables included in a surgical tool with a computer system, wherein the surgical tool is mounted to a tool driver, one or more segments are defined along a portion of at least one of the one or more drive cables, and each segment exhibits a usage value, and altering the usage value of at least one of the one or more segments based on usage of the surgical tool.

Each of embodiments A and B may have one or more of the following additional elements in any combination: Element 1: further comprising altering the usage value of the at least one of the one or more segments based on movement of the one or more drive cables corresponding to the at least one of the one or more segments. Element 2: wherein the surgical tool further includes a drive housing having one or more drive inputs matable with a corresponding one or more drivers provided on the tool driver, the method further comprising actuating at least one of the one or more drivers based on a signal received from the computer system and thereby causing actuation of at least one of the one or more drive inputs, linearly moving at least one of the one or more drive cables as acted upon by the at least one of the one or more drive inputs, measuring tensile loading on the at least one of the one or more drive cables with a torque sensor in communication with the computer system, and increasing the usage value of the at least one of the one or more segments with the computer system based on tensile data received from the torque sensor. Element 3: further comprising increasing the usage value of the at least one of the one or more of segments proportional to a magnitude of the tensile data. Element 4: wherein the surgical tool further includes a drive housing having one or more drive inputs matable with a corresponding one or more drivers provided on the tool driver, the method further comprising actuating at least one of the one or more drivers based on a signal received from the computer system and thereby causing rotation of at least one of the one or more drive inputs, linearly moving at least one of the one or more drive cables as acted upon by the at least one of the one or more drive inputs, measuring a rotational output of one of the one or more drive inputs or one of the one or more drivers with a rotary encoder in communication with the computer system, determining a linear distance traveled by the at least one of the one or more segments with the computer system based on rotational output data received from the rotary encoder, and increasing the usage value of the at least one of the one or more segments based on the linear distance traveled. Element 5: wherein the surgical tool further includes a wrist having first and second sets of pulleys that define an S-bend through which the one or more drive cables extend, the method further comprising moving the at least one of the one or more segments at least partially through the S-bend over the linear distance, and increasing the usage value based on full bending reversal or partial bending reversal of the at least one of the one or more segments traversing the S-bend. Element 6: further comprising increasing the usage value of the at least one of the one or more segments proportional to a magnitude of bending forces assumed by the at least one of the one or more segments linearly traversing the S-bend. Element 7: further comprising aggregating usage value increments with the computer system to determine a current usage value of the at least one of the one or more segments. Element 8: further comprising calculating when at least one of the one or more drive cables will fail based on the current usage value of the at least one of the one or more segments. Element 9: further comprising issuing an alert with the computer system when the current usage value reaches a predetermined usage value for at least one of the at least one of the one or more segments. Element 10: further comprising preventing the surgical tool from being used in a subsequent procedure when the current usage value reaches a predetermined usage value for at least one of the at least one of the one or more segments. Element 11: further comprising increasing the usage value of the at least one of the one or more segments based on a non-operational procedure selected from the group consisting of an autoclave cycle, an amount of time the surgical tool is mounted to the tool driver, a number of times the surgical tool is mounted to and detached from the tool driver, a number of procedures undertaken by the surgical tool, and any combination thereof.

Element 12: wherein the surgical tool further includes a drive housing having one or more drive inputs matable with a corresponding one or more drivers provided on the tool driver, wherein the instructions for execution by the processor for performing the method further comprise actuating at least one of the one or more drivers based on a signal received from the computer system and thereby causing actuation of at least one of the one or more drive inputs, linearly moving at least one of the one or more drive cables as acted upon by the at least one of the one or more drive inputs, measuring tensile loading on the at least one of the one or more drive cables with a torque sensor in communication with the computer system, and increasing the usage value of the at least one of the one or more segments with the computer system based on tensile data received from the torque sensor. Element 13: wherein the surgical tool further includes a drive housing having one or more drive inputs matable with a corresponding one or more drivers provided on the tool driver, wherein the instructions for execution by the processor for performing the method further comprise actuating at least one of the one or more drivers based on a signal received from the computer system and thereby causing rotation of at least one of the one or more drive inputs, linearly moving at least one of the one or more drive cables as acted upon by the at least one of the one or more drive inputs, measuring a rotational output of one of the one or more drive inputs or one of the one or more drivers with a rotary encoder in communication with the computer system, determining a linear distance traveled by the at least one of the one or more segments with the computer system based on rotational output data received from the rotary encoder, and increasing the usage value of the at least one of the one or more segments based on the linear distance traveled. Element 14: wherein the surgical tool further includes a wrist having first and second sets of pulleys that define an S-bend through which the one or more drive cables extend, wherein the instructions for execution by the processor for performing the method further comprise moving the at least one of the one or more segments at least partially through the S-bend over the linear distance, and increasing the usage value based on full bending reversal or partial bending reversal of the at least one of the one or more segments traversing the S-bend. Element 15: wherein the instructions for execution by the processor for performing the method further comprise aggregating usage value increments with the computer system to determine a current usage value of the at least one of the one or more segments. Element 16: wherein the instructions for execution by the processor for performing the method further comprise calculating when at least one of the one or more drive cables will fail based on the current usage value of the at least one of the one or more segments. Element 17: wherein the instructions for execution by the processor for performing the method further comprise issuing an alert with the computer system when the current usage value reaches a predetermined usage value for at least one of the at least one of the one or more segments. Element 18: wherein the instructions for execution by the processor for performing the method further comprise preventing the surgical tool from being used in a subsequent procedure when the current usage value reaches a predetermined usage value for at least one of the at least one of the one or more segments.

By way of non-limiting example, exemplary combinations applicable to A and B include: Element 2 with Element 3; Element 4 with Element 5; Element 5 with Element 6; Element 7 with Element 8; Element 7 with Element 9; Element 7 with Element 10; Element 15 with Element 16; Element 15 with Element 17; and Element 15 with Element 18.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A method of operating a surgical tool, comprising:
   mounting the surgical tool to a tool driver, the surgical tool including a drive cable movable to actuate an end effector, wherein a plurality of discrete segments are defined along a contiguous portion of the drive cable and each segment exhibits a usage value corresponding to a lifetime operational usage of the corresponding segment based at least partially on tensile loading on the drive cable assumed by the corresponding segment;
   monitoring usage of the drive cable with a computer system in communication with the tool driver; and
   altering the usage value of at least one of the plurality of discrete segments based on usage of the surgical tool.

2. The method of claim 1, further comprising altering the usage value of the at least one of the plurality of discrete segments based on movement of the drive cable.

3. The method of claim 1, wherein the surgical tool further includes a drive housing having a drive input matable with a driver provided on the tool driver, the method further comprising:
   actuating the driver based on a signal received from the computer system and thereby causing actuation of drive input;
   linearly moving the drive cable as acted upon by the drive input;
   measuring the tensile loading on the drive cable with a torque sensor in communication with the computer system; and
   increasing the usage value of the at least one of the plurality of discrete segments with the computer system based on tensile data received from the torque sensor.

4. The method of claim 3, further comprising increasing the usage value of the at least one of the plurality of discrete of segments proportional to a magnitude of the tensile data.

5. The method of claim 1, wherein the surgical tool further includes a drive housing having a drive input matable with a driver provided on the tool driver, the method further comprising:
   actuating the driver based on a signal received from the computer system and thereby causing rotation of drive input;
   linearly moving the drive cable as acted upon by the drive input;
   measuring a rotational output of the drive input or the driver with a rotary encoder in communication with the computer system;
   determining a linear distance traveled by the at least one of the plurality of discrete segments with the computer system based on rotational output data received from the rotary encoder; and
   increasing the usage value of the at least one of the plurality of discrete segments based on the linear distance traveled.

6. The method of claim 5, wherein the surgical tool further includes a wrist having first and second sets of pulleys that define an S-bend through which the drive cable extends, the method further comprising:
   moving the at least one of the plurality of discrete segments at least partially through the S-bend over the linear distance; and
   increasing the usage value based on full bending reversal or partial bending reversal of the at least one of the plurality of discrete segments traversing the S-bend.

7. The method of claim 6, further comprising increasing the usage value of the at least one of the plurality of discrete segments proportional to a magnitude of bending forces assumed by the at least one of the plurality of discrete segments linearly traversing the S-bend.

8. The method of claim 1, further comprising aggregating usage value increments with the computer system to determine a current usage value of the at least one of the plurality of discrete segments.

9. The method of claim 8, further comprising calculating when the drive cable will fail at the at least one of the plurality of discrete segments based on the current usage value of the at least one of the plurality of discrete segments.

10. The method of claim 8, further comprising issuing an alert with the computer system when the current usage value reaches a predetermined usage value for at least one of the at least one of the plurality of discrete segments.

11. The method of claim 8, further comprising preventing the surgical tool from being used in a subsequent procedure when the current usage value reaches a predetermined usage value for at least one of the at least one of the plurality of discrete segments.

12. The method of claim 1, further comprising increasing the usage value of the at least one of the plurality of discrete segments based on a non-operational procedure selected from the group consisting of an autoclave cycle, an amount of time the surgical tool is mounted to the tool driver, a number of times the surgical tool is mounted to and detached from the tool driver, a number of procedures undertaken by the surgical tool, and any combination thereof.

13. A non-transitory medium readable by a processor and storing instructions for execution by the processor for performing a method comprising:
   monitoring usage of a drive cable included in a surgical tool with a computer system, wherein the surgical tool is mounted to a tool driver and a plurality of discrete segments are defined along a contiguous portion of least the drive cable, and wherein each segment exhibits a usage value corresponding to a lifetime operational usage of the corresponding segment based at least partially on tensile loading on the drive cable assumed by the corresponding segment; and
   altering the usage value of at least one of the plurality of discrete segments based on usage of the surgical tool.

14. The non-transitory medium of claim 13, wherein the surgical tool further includes a drive housing having a drive input matable with a driver provided on the tool driver, and wherein the instructions for execution by the processor for performing the method further comprise:
   actuating the driver based on a signal received from the computer system and thereby causing actuation of the drive input;
   linearly moving the drive cable as acted upon by the drive input;
   measuring the tensile loading on the drive cable with a torque sensor in communication with the computer system; and
   increasing the usage value of the at least one of the plurality of discrete segments with the computer system based on tensile data received from the torque sensor.

15. The non-transitory medium of claim 13, wherein the surgical tool further includes a drive housing having a drive input matable with a driver provided on the tool driver, and wherein the instructions for execution by the processor for performing the method further comprise:
   actuating the driver based on a signal received from the computer system and thereby causing rotation of the drive input;
   linearly moving the drive cable as acted upon by the drive input;
   measuring a rotational output of the drive input or the driver with a rotary encoder in communication with the computer system;
   determining a linear distance traveled by the at least one of the plurality of discrete segments with the computer system based on rotational output data received from the rotary encoder; and
   increasing the usage value of the at least one of the plurality of discrete segments based on the linear distance traveled.

16. The non-transitory medium of claim 13, wherein the surgical tool further includes a wrist having first and second sets of pulleys that define an S-bend through which the drive cable extends, wherein the instructions for execution by the processor for performing the method further comprise:
   moving the at least one of the plurality of discrete segments at least partially through the S-bend over the linear distance; and
   increasing the usage value based on full bending reversal or partial bending reversal of the at least one of the plurality of discrete segments traversing the S-bend.

17. The non-transitory medium of claim 13, wherein the instructions for execution by the processor for performing the method further comprise aggregating usage value increments with the computer system to determine a current usage value of the at least one of the plurality of discrete segments.

18. The non-transitory medium of claim 17, wherein the instructions for execution by the processor for performing the method further comprise calculating when the drive cable will fail based on the current usage value of the at least one of the plurality of discrete segments.

19. The non-transitory medium of claim 17, wherein the instructions for execution by the processor for performing the method further comprise issuing an alert with the computer system when the current usage value reaches a predetermined usage value for at least one of the at least one of the plurality of discrete segments.

20. The non-transitory medium of claim 17, wherein the instructions for execution by the processor for performing the method further comprise preventing the surgical tool from being used in a subsequent procedure when the current usage value reaches a predetermined usage value for at least one of the at least one of the plurality of discrete segments.

* * * * *